United States Patent [19]

Koga et al.

[11] Patent Number: 5,304,378
[45] Date of Patent: Apr. 19, 1994

[54] WOUND DRESSING MATERIAL

[75] Inventors: Joichi Koga; Koichi Nomura, both of Sakai; Hiroshi Hojo, Kounan, all of Japan

[73] Assignee: Niigata Hi-Spinners Ltd., Iwafune, Japan

[21] Appl. No.: 736,143

[22] Filed: Jul. 26, 1991

[30] Foreign Application Priority Data

Jul. 26, 1990 [JP] Japan .................................. 2-198672

[51] Int. Cl.⁵ ............................................. A61F 13/00
[52] U.S. Cl. ..................................... 424/445; 424/443; 424/444; 424/543; 8/128.1
[58] Field of Search ............... 424/443, 444, 445, 543; 8/128.1, 127.51, 127.5, 128.3

[56] References Cited

U.S. PATENT DOCUMENTS

| | | | |
|---|---|---|---|
| 4,396,388 | 8/1983 | Hojo et al. | 8/128.3 |
| 4,570,629 | 2/1986 | Widra | 604/368 |
| 4,957,795 | 9/1990 | Riedel | 428/74 |

FOREIGN PATENT DOCUMENTS 0002583 of 1864 United Kingdom ............... 424/445

Primary Examiner—Thurman K. Page
Assistant Examiner—James M. Spear
Attorney, Agent, or Firm—Armstrong, Westerman, Hattori, McLeland & Naughton

[57] ABSTRACT

A novel wound dressing material is produced by a chemical treatment of animal fibers, particularly, wool, to strip off the keratin layers of the surfaces of the fibers so as to expose the non-keratin protein in the underlayers, which is hydrophilic. The wound dressing material provides healing and regenerating effects on the wounds, and can be produced at a low cost.

2 Claims, No Drawings

WOUND DRESSING MATERIAL

BACKGROUND OF THE INVENTION

Field of the Invention

The present invention relates to an improvement in a wound dressing material used for healing a wound of a patient.

State of the Art

In case that the skin is damaged by wounds including cuts and burns, various man-made dressing materials are used to heal the wounds.

The wound dressing materials made of synthetic materials are those of, such as silicone compounds, nylon fabrics, or petrolatum gauzes and the like. These conventional wound dressing materials are inexpensive and easily available, however, they are poor in affinity with the wounded area, and dissatisfactory from the view point of healing the wounded.

Thus, in order to obtain high-performance wound dressing materials, it is necessary to use natural materials having properties similar to those of the patients' skin. To this end, heretofore, there have been provided lyophilized hog skins and non-woven fabric made of fibrous atelocollagen produced by alkali-treatment of the corium collagen of cattle. These conventional wound dressings are, however, still insufficient in vapor permeability and antibacterial properties. In addition, it is difficult to assure uniform quality of the conventional wound dressings in manufacturing, which makes the price of these conventional wound dressing materials high, and therefore, use of the materials is limited.

As for a combination of synthetic materials and natural materials used in the wound dressings, Japanese Patent Publication No. 47470/1988 discloses a film produced from keration through solubilization of the keratin and graft-copolymerization of the thus solubilized keration with water-soluble polymers. Such a film is similar in composition to an organism or patients' skin, but due to deformation in the chemical structure, it is not expected for the film to provide the same properties as those of native products.

SUMMARY OF THE INVENTION

In view of the prior art described above, it is the object of the present invention to provide a wound dressing material which is excellent in vapor permeability and antibacterial properties as is in case of the natural materials, and which can be produced at a low cost and easily handled while assured in quality to be uniform.

The wound dressing materials according to the present invention is made of animal-fibered fabric, wherein keratin layers of the surfaces of the animal fibers are stripped off through a chemical treatment to expose the non-keratin protein in the underlayer, whereby the surfaces of the animal fibers are modified to be hydrophilic.

DETAILED EXPLANATION OF THE PREFERRED INVENTION

In the wound dressing material of the present invention, it is preferable to use wool as the animal fibers, because wool is easily available and its processing techniques are well established.

Some of the methods for stripping off the keratin layers from the surfaces of the animal fibers are disclosed in Japanese Patent Nos. 1164876 and 1454499, the former of which was invented by one of the inventors of the present invention, and the latter was invented by one of the inventors of the present invention and his co-inventors.

Further, it is preferable for the present invention to use the latest method disclosed in Japanese Patent Application No. 25859/1990, in which method a series of the steps as follows is performed: a mechanical strain such as that caused by rapid bending and stretching is produced in wool in a water bath containing a small amount of an electrophilic reagent such as Lewis acids so as to swell chemically active non-keratin protein existing in the vicinity of the surface layer of wool selectively, thereafter, the Lewis acids are applied to the swelled non-keratin protein of the wool so that the protein of the wool may lose its activity and the protein may serve as a temporary barrier, and then, under acidic condition, an oxidizing agent is applied to the surface of the wool to have the keratin layers existing in the surface layers of the wool rapidly stripped off therefrom, and at the same time, the Lewis acids applied to the wool are removed therefrom through oxidation performed under the acidic condition, and the oxidation reaction is interrupted and the wool is washed.

The above treatment may be carried out under a condition in which the wool is still not woven, and the wool may be woven into fabrics after the treatment. However, it is generally preferable to perform the treatment under a condition in which the wool is woven fabrics.

In order to heal a damaged part of an organism or a patient, heretofore, similar part of an animal corresponding to the damaged part of the patient has been used. Thus, as for a wounded skin of the patient, it is in accordance with the same idea as the above to use the wound dressing materials made of the skins of mammals for healing.

On the other hand, typical matter for protecting bare skin of animals is pelage or animal's fibers, which is called "a second skin". The present invention was made on this basis.

However, each of the animal fibers has its outer peripheral surface covered with keratin which is a scleroprotein, and, when the animal fibers as obtained woven or knitted into fabrics, such fabrics are not adequate for a material for dressing the wound. This is due to the fact that corneums or horny tissues of the animal fibers repel water to make the animal fibers hydrophobic, and that the animal fibers are poor in affinity with the wounded area. It has been found that, even when keration fibers are solubilized by using hydrogen-bonding destroying agents and reducing agents and formed into a film, it is impossible for the film to sufficiently function of healing the wound because such a film has its native chemical structure deformed.

In view of these facts, the inventors of the present invention expected that, when the keratin layers are stripped off from the surfaces of the animal fibers to expose their hydrophilic layers, these hydrophilic layers may show much affinity with the wounded area, and carried out several experiments. Having obtained good experimental results, the inventors established the present invention.

EXAMPLE

A piece of moslin woolen fabric (specified in JIS-0803-1980, having a size of 1/52×68/1 and a weight of 102+5 g) was immersed in a bath of a solution of hydrochloric acid saturated with purified salt, and then subjected to a mechanical bending-and-stretching treatment for a period of from 2 to 3 minutes in the bath. After that, the treated piece of woolen fabric was dehydrated, and then immersed in a bath of an aqueous solution of hypochlorous acid (containing 4% o.w.f. active chlorine) while subjected to further mechanical treatments similar to the above, whereby keratin layers existing in the surfaces of the wool were stripped off.

The piece of the treated fabric was then immersed in an acidic sodium sulfite solution to stop the oxidation, and washed repeatedly, and thereafter dried. The dried piece of woolen fabric was thoroughly washed in physiological saline.

In the above process, in place of the solution of hydrochloric acid saturated with the purified salt, it is possible to use a very dilute solution (20 to 50 ppm) of electrophilic reagents such as chlorides or acetates of cobalt (Co) and nickel (Ni). In this case it is necessary to add the step of treating the piece of woolen fabric in another bath containing inorganic acid at a low concentration after treating in the above oxidation-stopping bath, so as to remove the above metals from the piece of woolen fabric.

The wound dressing material of the present invention prepared as above was tested to determine the affinity with an organism in the following manner:

In the following test, seventy rats (Jbc-Wister rat) each of which was a 90 day old were used as laboratory animals. These rats were divided into the following four groups, depending on the test materials.

(Group 1)
for testing the moslin woolen fabric (hereinafter referred to simply as the "woolen fabric") which is a starting material of the wound dressing material of the present invention;

(Group 2)
for testing the wound dressing material of the present invention (hereinafter referred to as the "fabric of the invention");

(Group 3)
for testing a S-cyanoethylated keratin film (hereinafter referred to as the "keratin film") which was cast from a formic acid solution; and (Group 4)
for testing a sterilized and lyophilized hogskin corium (hereinafter referred to as the "hog skin") which is commercially available.

Each of the above Groups 1 to 4 contained fifteen rats, and was subdivided into three subgroups each of which contained five rats.

The entire body of each of the rats was anesthetized. Then, the rats received a round-shaped cut (having a diameter of 2.0 cm) in its back median skin to form an incised skin wound.

On the other hand, round test pieces (having a diameter of 3.0 cm) of each of testing materials were cut out of the materials which were immersed in a sterilized physiological saline, and the skin wounds were covered with the test pieces. At this time, a super glue or instant adhesive was applied to the back of the rat in its annular skin zone bordering the wound so as to prevent the test piece from falling off.

Healing effects of each of the test pieces on the wounds were observed with time through the naked eye. Some of the rats were killed after 3 and 7 days to obtain tissue samples of the wounds. The obtained tissue samples were fixed with formalin, and then embedded in paraffin, and the samples were then cut into microsections, each of which had a thickness of 6 microns. Each of the microsections was stained to facilitate the microscopic observation. In the naked eye observation, surface condition, amount of exudate and scab formation of each of the wounds were observed. Contraction rates in area of each of the wounds were determined by measuring an area of each of the wounds at intervals of predetermined period of days. Also, the adhesive properties of each of the test pieces and a period of time required for complete remedy. The complete remedy means a condition in which the lost skin was completely regenerated to close the wound completely, and the scab formed on the wound completely fell off.

Results of the Naked Eye Observation

The wounds varied in appearance and internal condition with time, giving the data as shown in Table 1.

Findings of the tissues are shown in Table 2.

TABLE 1

| Test Group | Day of observation | Exudate Storage | Scab Formation | Contr'n of Wounds | Contr'n rate % |
|---|---|---|---|---|---|
| 1 | 3rd day | + | unclear | − | 0.1 |
|   | 1 week | + | unclear | + |  |
| 2 | 3rd day | + | + | + | 21.0 |
|   | 1 week | − | + | + |  |
| 3 | 3rd day | ++ | − | − | 8.2 |
|   | 1 week | + | ++ | ++ |  |
| 4 | 3rd day | + | − | + | 17.5 |
|   | 1 week | + | − | + |  |

−: non
+: small
+: normal
++: large

TABLE 2

| Test Group | Decomposition of Materials | Amount of Exudate | Blastema Formation | Epithelian Regeneration |
|---|---|---|---|---|
| 1 | good | large | poor | poor |
| 2 | better | small | good | good |
| 3 | bad | largest | bad | poor |
| 4 | poor | large | poor | good |

Group 1 (Woolen Fabrics)

In the naked eye observation, the contraction of the wounds was poor on both the third and the seventh day, and the period required for complete regeneration of the lost skin of the wounds was long. This is probably due to the fact that the woolen fabrics of the test piece cannot sufficiently absorb the exudate issued from the wounds in the initial stage and that the woolen fabrics of the test piece stick to the wounds.

Based on the observation of the tissues of the wounds, it was found on the third day that there was a large storage of the exudate under the test piece, the exudate being issued from inflammatory tissues; and that the epithelial regeneration was poor. On the seventh day, it was clearly observed that fibers of the test piece were separated from each other, that neutrophils were deposited on these fibers, that decomposition absorption of these fibers of the test piece was promoted, and that purulent nidi and hemorrhagic nidi existed so as to prevent the blastema formation (i.e., fibrosing) from being promoted.

Group 2 (Fabric of the Invention)

Contraction of the wound was clearly observed on the third day. This is probably due to the fact that the fabric of the invention is excellent in properties of absorbing and drying the exudate tissues and sufficiently absorbed the exudate from the wound of the initial stage. It was also observed that a thin scab was formed over a large area of the wound under the test piece to promote regeneration of the epithelium or skin.

Based on the observation of the tissues, it was found that the decomposition absorption of the fibers of the test piece was most promoted, and regeneration of the epithelium was also promoted. Although normal congestion and bleeding were observed at the earlier stages, it was found on the seventh day and later that the blastema formation (i.e., fibrosing) was promoted under the scab, and a plenty of finer blood vessels were newly generated. Further, regeneration of the epithelium (i.e., skin) over the entire area of the wound was found good.

Group 3 (Keratin Film)

Although the contraction rate in area of the wound was still small on the third day, but was remarkably improved on the seventh day. The reason is considered to be that, since the keratin film of the test piece is poor in moisture-absorbtion and is irritative, a large storage of the exudate appears in a relatively earlier stage of the wound, and, since the keration film tends to be harder and too brittle, the test piece of the keration film covering the wound is broken at a relatively earlier stage of the wound to enhance the contraction of the wound drastically.

Based on the observation of the wounded tissues, no decomposition absorption of the test piece was found, and the test piece stuck to the entire surface of the wound. Probably due to the above, a large storage of the exudate was found. Even on the seventh day, the blastema formation (i.e., fibrosing) in the wounded tissues was still poor such as was found in case of the woolen fabric, and the congestion and bleeding remarkably occurred while an amount of the exudate still increased.

Group 4 (Hog Skin)

Contraction of the wound was found to be favorably promoted. Although the scab formed on the wound was thick and hard, it was supposed that the healing under the scab was smoothly promoted.

Based on the observation of the wounded tissues, it was found that, though no absorption of the hog skin was observed, there were produced a plenty of hair cracks and roughed areas in the test piece, through which it was supposed that the hog skin was being gradually decomposed. In the central area of the wound, it was found that the amount of initial bleeding was large, the amount of the exudate observed on the seventh day and later was also large, the blastema formation (i.e., fibrosing) in the wounded tissues was poor, but that the regeneration of the epithelium in the area bordering the wound tissues was remarkably promoted.

The wound dressing material of the present invention provides healing and regenerating effects on the patient's wound, the effects being superior to those of the conventional hog skin heretofore widely used by clinicians in hospitals.

The starting material of the wound dressing material of the present invention is wool fibers, which are easily available, and enables the user to select them in respect of length and fineness of the fiber, fineness and twist of the yarn and strand, suitable weaving and knitting type, and fabric density, whereby it is possible to produce the products having desirable properties such as contraction/expansion properties. In addition, the steps of the above processing can be easily carried out by using the conventional techniques widely used in the textile industry. Therefore, it is possible to provide the wound dressing material of the present invention at a low cost, which is equivalent to one several tenths of the cost of the conventional material made of the hog skin.

We claim:

1. A wound dressing material made of animal-fibered fabric, wherein keratin layers of the surfaces of the animal fibers are stripped off through a chemical treatment to expose the non-keratin protein in the underlayers, whereby the surfaces of the animal fibers are modified to be hydrophilic, wherein said chemical treatment comprises
   (i) placing said animal fibers in an aqueous solution comprising water and an electrophilic reagent,
   (ii) applying a mechanical strain consisting essentially of rapid bending and stretching to said animal fibers which is effective to selectively swell non-keratin protein located beneath the surfaces of said animal fibers.
   (iii) applying an oxidizing agent to said animal fibers in an amount effective to remove said keratin layers.

2. The wound dressing material of claim 1, wherein wool is used as the animal fibers of the fabric.

* * * * *

UNITED STATES PATENT AND TRADEMARK OFFICE
CERTIFICATE OF CORRECTION

PATENT NO.: 5,304,378
DATED : Apr. 19, 1994
INVENTOR(S): KOGA et al

It is certified that error appears in the above-identified patent and that said Letters Patent is hereby corrected as shown below:

Cover page, change "[73] Assignee: Niigata Hi-Spinners Ltd., Iwafune, Japan" to read: --[73] Assignee: Hojo, Hiroshi, Kounan-shi Signed and Sealed this Twenty-third Day of May, 1995

Attest:

BRUCE LEHMAN

Attesting Officer  Commissioner of Patents and Trademarks